(12) United States Patent
Davis et al.

(10) Patent No.: US 10,599,813 B2
(45) Date of Patent: Mar. 24, 2020

(54) INTELLIGENT ROUTER FOR MEDICAL PAYMENTS

(71) Applicant: ELECTRONIC COMMERCE FOR HEALTHCARE ORGANIZATIONS, INC., Westlake, OH (US)

(72) Inventors: Ryan J. Davis, Fairview, OH (US); Timothy S. Adkins, Hudson, OH (US); Kristopher T. Kern, Strongsville, OH (US); Charles E. Kirkpatrick, Cypress, TX (US); William H. Davis, Fairview Park, OH (US)

(73) Assignee: ELECTRONIC COMMERCE FOR HEALTHCARD ORGANIZATIONS, INC., Westlake, OH (US)

( * ) Notice: Subject to any disclaimer, the term of this patent is extended or adjusted under 35 U.S.C. 154(b) by 0 days.

(21) Appl. No.: 14/095,080

(22) Filed: Dec. 3, 2013

(65) Prior Publication Data

US 2014/0095195 A1    Apr. 3, 2014

Related U.S. Application Data

(63) Continuation of application No. 13/334,312, filed on Dec. 22, 2011, now Pat. No. 8,626,536, which is a continuation-in-part of application No. 10/930,499, filed on Aug. 31, 2004, now abandoned.

(51) Int. Cl.
*G06Q 40/08* (2012.01)
*G06F 19/00* (2018.01)

(52) U.S. Cl.
CPC ........... *G06F 19/328* (2013.01); *G06Q 40/08* (2013.01)

(58) Field of Classification Search
CPC ........ G06Q 40/08; G06Q 40/00; G06Q 40/12; G06Q 40/02; G06F 19/328
See application file for complete search history.

(56) References Cited

U.S. PATENT DOCUMENTS

| 3,679,175 A | 7/1972 | Drayton |
|---|---|---|
| 3,921,196 A | 11/1975 | Patterson |

(Continued)

FOREIGN PATENT DOCUMENTS

| EP | 1049056 A2 | 11/2000 | |
|---|---|---|---|
| JP | 2006085385 A | 3/2006 | |
| JP | 2008269191 A | 11/2008 | |
| WO | 2002084438 A2 | 10/2002 | |
| WO | 2003088078 A2 | 10/2003 | |
| WO | WO-03088124 A2 * | 10/2003 | ............. G06Q 10/10 |
| WO | 2008111094 A2 | 9/2008 | |

OTHER PUBLICATIONS

Stribling, D.: Checks Vs. Bank Drafts.*

(Continued)

*Primary Examiner* — Bijendra K Shrestha
(74) *Attorney, Agent, or Firm* — Fay Sharpe LLP

(57) ABSTRACT

One or more servers (70) are configured to periodically format (90, 92) and send (94) payments (26) to a payee. According to an exemplary embodiment, the payments (26) include a consolidated financial instrument (73) and at least one explanation of explanation of benefit (75) associated with the consolidated financial instrument. The consolidated financial instrument (73) transfers accumulated monies without co-mingling funds in compliance with ERISA regulations. According to an exemplary embodiment, the at least one associated explanation of benefit (75) includes a patient identification, a payer identification, a service provider identification, a date of service, a service identification, a patient obligation, and an amount paid. Acceptance of the payment to each payee is recorded (100) in a data store (102).

11 Claims, 5 Drawing Sheets

(56) References Cited

U.S. PATENT DOCUMENTS

| | | | |
|---|---|---|---|
| 3,935,427 | A | 1/1976 | Geul |
| 4,135,241 | A | 1/1979 | Stanis et al. |
| 4,212,069 | A | 7/1980 | Baumann |
| 4,247,759 | A | 1/1981 | Yuris et al. |
| 4,277,837 | A | 7/1981 | Stuckert |
| 4,319,225 | A | 3/1982 | Klose |
| 4,346,442 | A | 8/1982 | Musmanno |
| D266,512 | S | 10/1982 | Fubershaw et al. |
| 4,359,631 | A | 11/1982 | Lockwood et al. |
| 4,360,875 | A | 11/1982 | Behnke |
| 4,370,649 | A | 1/1983 | Fuerle |
| 4,408,181 | A | 10/1983 | Nakayama |
| 4,454,414 | A | 6/1984 | Benton |
| 4,491,725 | A | 1/1985 | Pritchard |
| D284,193 | S | 6/1986 | Marshall |
| 4,632,428 | A | 12/1986 | Brown |
| 4,648,037 | A | 3/1987 | Valentino |
| D289,762 | S | 5/1987 | Alterio et al. |
| 4,667,292 | A | 5/1987 | Mohlenbrock |
| D292,403 | S | 10/1987 | Renard |
| 4,858,121 | A | 8/1989 | Barber et al. |
| D306,854 | S | 3/1990 | Davis et al. |
| 4,974,878 | A * | 12/1990 | Josephson .......... B42D 15/0053 283/58 |
| 5,590,196 | A | 12/1996 | Moreau |
| 5,644,778 | A | 7/1997 | Burks et al. |
| 5,677,955 | A | 10/1997 | Doggett et al. |
| 5,748,907 | A | 5/1998 | Crane |
| 5,832,460 | A | 11/1998 | Bednar et al. |
| 5,884,271 | A | 3/1999 | Pitroda |
| 5,890,129 | A | 3/1999 | Sprugeon |
| 6,003,007 | A | 12/1999 | Dirienzo |
| 6,012,035 | A | 1/2000 | Freeman, Jr. et al. |
| 6,088,677 | A | 7/2000 | Spurgeon |
| 6,208,973 | B1 * | 3/2001 | Boyer .................. G06Q 20/02 705/2 |
| 6,311,170 | B1 * | 10/2001 | Embrey ................ G06Q 20/02 705/39 |
| 6,343,310 | B1 | 1/2002 | Dirienzo |
| 6,662,999 | B1 | 12/2003 | Vancour et al. |
| 6,827,260 | B2 | 12/2004 | Stoutenburg et al. |
| 7,039,593 | B2 | 5/2006 | Sagar |
| 7,066,382 | B2 | 6/2006 | Kaplan |
| 7,380,707 | B1 | 6/2008 | Fredman |
| 7,383,223 | B1 | 6/2008 | Dilip |
| 7,493,266 | B2 * | 2/2009 | Gupta .................. 705/3 |
| 7,593,266 | B2 * | 9/2009 | Senoo .................. G11C 16/3454 365/185.22 |
| 7,630,937 | B1 | 12/2009 | Mo |
| 7,661,586 | B2 | 2/2010 | Robbins, Jr. et al. |
| 7,672,858 | B2 | 3/2010 | Tolan et al. |
| 7,752,134 | B2 | 7/2010 | Spear |
| 7,769,604 | B1 | 8/2010 | Lefco et al. |
| 7,774,214 | B1 | 8/2010 | Lefco et al. |
| 7,783,504 | B1 | 8/2010 | Lefco et al. |
| 7,792,686 | B2 | 9/2010 | Allen |
| 7,792,749 | B2 | 9/2010 | Ganesan |
| 7,813,940 | B2 | 10/2010 | Ambrose |
| 7,853,524 | B2 | 12/2010 | Kight |
| 7,913,918 | B2 | 3/2011 | Zellner et al. |
| 7,949,580 | B1 | 5/2011 | Boyer et al. |
| 7,953,638 | B2 * | 5/2011 | Hofer .................. G06Q 30/08 705/26.1 |
| 8,015,029 | B2 | 9/2011 | Flood |
| 8,019,627 | B2 | 9/2011 | Baylor et al. |
| 8,078,481 | B2 | 12/2011 | Steinbarth et al. |
| 8,175,901 | B1 | 5/2012 | Lefco et al. |
| 8,204,766 | B2 | 6/2012 | Bush |
| 8,321,240 | B2 | 11/2012 | Lorsch |
| 8,655,688 | B1 | 2/2014 | Lefco et al. |
| 2001/0034618 | A1 | 10/2001 | Kessler et al. |
| 2002/0055858 | A1 | 5/2002 | Jackson |
| 2002/0062224 | A1 | 5/2002 | Thorsen et al. |
| 2002/0103680 | A1 | 8/2002 | Newman |
| 2002/0111916 | A1 | 8/2002 | Coronna |
| 2002/0138302 | A1 | 9/2002 | Bodnick |
| 2002/0147867 | A1 * | 10/2002 | Satlow .................. G06F 19/328 710/100 |
| 2002/0184148 | A1 * | 12/2002 | Kahn .................. G06Q 20/102 705/40 |
| 2002/0194027 | A1 * | 12/2002 | Smith .................. G06Q 50/22 705/2 |
| 2002/0198831 | A1 * | 12/2002 | Patricelli ............ G06Q 20/10 705/40 |
| 2003/0149594 | A1 | 8/2003 | Beazley et al. |
| 2003/0187695 | A1 | 10/2003 | Drennan |
| 2003/0200118 | A1 * | 10/2003 | Lee .................. G06Q 20/04 705/2 |
| 2004/0039693 | A1 | 2/2004 | Nauman et al. |
| 2004/0064386 | A1 * | 4/2004 | Goguen .................. G06Q 30/04 705/34 |
| 2004/0083123 | A1 | 4/2004 | Kim et al. |
| 2004/0133509 | A1 | 7/2004 | McCoy et al. |
| 2004/0153337 | A1 * | 8/2004 | Cruze .................. G06F 19/328 705/2 |
| 2004/0172309 | A1 | 9/2004 | Selwanes et al. |
| 2004/0172312 | A1 | 9/2004 | Selwanes et al. |
| 2004/0172313 | A1 | 9/2004 | Stein |
| 2004/0186744 | A1 | 9/2004 | Lux |
| 2004/0249745 | A1 | 12/2004 | Baaren |
| 2005/0010446 | A1 | 1/2005 | Lash et al. |
| 2005/0033604 | A1 | 2/2005 | Hogan |
| 2005/0033609 | A1 | 2/2005 | Yang |
| 2005/0071283 | A1 * | 3/2005 | Randle .................. G06Q 20/04 705/75 |
| 2005/0209964 | A1 | 9/2005 | Allen et al. |
| 2005/0228700 | A1 * | 10/2005 | Barcomb ................ G06Q 50/22 705/4 |
| 2005/0261944 | A1 | 11/2005 | Rosenberger |
| 2005/0288964 | A1 * | 12/2005 | Lutzen .................. G06F 19/328 705/2 |
| 2006/0010016 | A1 | 1/2006 | Kossol et al. |
| 2006/0036523 | A1 | 2/2006 | Stover et al. |
| 2007/0005402 | A1 | 1/2007 | Kennedy et al. |
| 2007/0005403 | A1 | 1/2007 | Kennedy et al. |
| 2007/0007335 | A1 | 1/2007 | Cracchiolo et al. |
| 2007/0043593 | A1 | 2/2007 | Provost et al. |
| 2007/0050205 | A1 | 3/2007 | Lieberman |
| 2007/0094047 | A1 | 4/2007 | Sager |
| 2008/0015982 | A1 | 1/2008 | Sokolic et al. |
| 2008/0033750 | A1 | 2/2008 | Burriss et al. |
| 2008/0133266 | A1 * | 6/2008 | Allen .................. G06Q 50/22 705/2 |
| 2008/0172248 | A1 | 7/2008 | Ambrose |
| 2008/0189185 | A1 | 8/2008 | Matsuo et al. |
| 2009/0119208 | A1 | 5/2009 | Cervenka |
| 2009/0222353 | A1 | 9/2009 | Guest et al. |
| 2010/0070301 | A1 | 3/2010 | Tolan et al. |
| 2010/0145848 | A1 | 6/2010 | Robbins, Jr. et al. |
| 2010/0257126 | A1 | 10/2010 | Tolan et al. |
| 2011/0251860 | A1 | 10/2011 | Boyer et al. |
| 2011/0288881 | A1 | 11/2011 | Machani et al. |
| 2011/0295614 | A1 | 12/2011 | Hummer et al. |
| 2011/0301972 | A1 | 12/2011 | Baylor et al. |
| 2012/0095787 | A1 | 4/2012 | Davis et al. |

OTHER PUBLICATIONS

Strbling, D: Checks, Vs. Bank Drafts, Dec. 25, 2009, p. 1.*
Strbling, D: Checks, Vs. Bank Drafts, Dec. 25, 2009, p. 1 (Year: 2009).*
Passport Health Plan: HIPPA—ASC X12N: Outbound EDI 835 Electronic Remittance Advice Transaction, Nov. 13, 2003, pp. 1-50 (Year: 2003).*
Committee of Health Plans and Healthcare Physicians/Providers: Coordination of Benefits: Tips for Payment Delays and Improving Accounts Receivables, Apr. 2004 (Year: 2004).*
Early Intervention Central Billing Office (EI-CBO): Billing Information for Providers, Jul. 2002, pp. 1-49 (Year: 2002).*
Datamation Aug. 1983 p. 219 "Telephone Terminal".

Computer Design Jul. 1982 p. 69 Fig. 2 "Compass Personal Computer".
Personal Computing Aug. 1985 p. 100 "Kaypro 2000 Computer".
Stribbling, D.: Checks Vs. Bank Drafts.
Hancock, et al.: "Payment Transactions, Instruments and System: A Survey", 1998, Journal of Banking & Finance 21; pp. 1573-1624.
Chakravorti, et al. "A Study of the Interrelated Bilateral Transactions in Credit Card Networks", Jul. 2001, Federal Reserve Bank of Chicago, pp. 1-41.
Sorkin, David E.:"Payment Methods for Consumer-to-Consumer Online Transactions", 2001, Akron Law Review, vol. 35:1, pp. 1-30.
Petition for Covered Business Method Review as Filed With the United States Patent Trial and Appeal Board in Re Post-Grant Review of Corresponding U.S. Pat. No. Re. 43,904 on Aug. 19, 2003.
Joint Claim Construction and Prehearing Statement, *Stoneeagle Services, Inc.* v. *Gillman, et al.*, Civil Docket No. 3:11-CV-2408-P-BD (N.D. Texas).
AP Vpayment XML Supplier Training, GE Corporate Payment Services, Dated Jan. 26, 2005.
Visa Commercial Solutions: Merchant Category Codes for IRS Form 1099-MISC Reporting, Visa USA Inc. 2004.
International Search Report, PCT Application No. PCT/US2012/042134, dated Dec. 13, 2012.
Jopari Solutions Press Releases Mar. 2005 to Aug. 2006 (26Pgs) From www.jopari.com Under the "Press" Tab.
U.S. Appl. No. 13/495,056, filed Jun. 13, 2012.
ECHO Health, Inc. "Electronic Commerce for Healthcare Organizations—Administering Healthcare Benefits, Profitably", Summer 1998, Sections I-VII—22 pgs.

* cited by examiner

INTELLIGENT ROUTER FOR MEDICAL PAYMENTS

The present application is a continuation of and claims the benefit of U.S. patent application Ser. No. 13/334,312, filed Dec. 22, 2011, now U.S. Pat. No. 8,626,536, which is a continuation-in-part of and claims the benefit of U.S. patent application Ser. No. 10/930,499, filed Aug. 31, 2004, now abandoned.

BACKGROUND

The present invention pertains to the payment of insurance, particularly medical insurance claims.

Currently, there are thousands of medical health insurance plans. Major employers negotiate custom medical insurance plans for their employees. Other companies select one of several insurance plans offered by an insurance company which may or may not include various options. Small business associations negotiate yet other health insurance contracts. The employees within these various employer groups obtain medical services at a plurality of covered medical facilities. Conversely, the various medical facilities treat patients with a myriad of different health plans.

The Employee Retirement Income Security Act (ERISA) prohibits the co-mingling of health insurance payments. A single instrument, such as a check, cannot be issued that shares risk. This results in insurance companies issuing a very large number of checks, and medical providers receiving large numbers of checks. Fulfillment vendors function as a go-between between the payers and the medical service providers. However, they too are bound by the ERISA rules against co-mingling of funds and must take care to avoid co-mingling funds received from payers and print or produce a multitude of checks to the various medical providers. Typically, a fulfillment vendor must send a medical provider a different and separate check for funds from each payer.

The funds are accompanied by an Explanation of Benefits (EOB) which is formatted and the contents normalized to the ANSI-835 standard. However, the normalized content is not standardized from employer group to employer group. Even though the normalized content may specify such terms as "non-covered" or "pending", different health insurance contracts give different meanings to these terms. For example, a "non-covered" service in from one contract can mean that the service provider must write-off the amount while in another contract the insured is responsible for payment of the "non-covered" amount. Secondary insurers add other possible interpretations of "non-covered". It is often difficult for the medical provider to determine, to a certainty, such simple information as the patient's co-pay, what amounts may be billed to the patient, which amounts must be written off, and the like. Determining this information generally requires a custom interpretation of the EOB from each of the various employer groups. Such individual interpretation is labor-intensive and expensive to the medical service providers. Moreover, due to the uncertainty regarding which charges must be written off and which may be billed to the patient, patients are often billed for charges which their insurance contract requires to be written off.

Only certain financial instruments meet ERISA regulations against co-mingling of funds. Certain legal entities such as trusts may be required for use of certain financial instruments. In addition, not all payees accept all types of financial instruments. Some financial instruments require electronic methods and access to certain networks and/or servers. Furthermore the financial instrument used to move funds and the EOB are intrinsically linked. A particular financial instrument may require a specific type of format for transmission of associated EOBs. As new financial instruments are developed and/or options for EOB formats permitted, system complexity for incorporation of new payment methods grows quickly.

A medical claims processing system typically implements one or several methods of payment. As new payment methods are developed, and the cost structure becomes more attractive, payers purchase or subscribe to these new payment methods with additional systems and/or subscriptions. However, interfaces between systems or providers for access to alternative methods add cost and complexity to tracking of payments and EOBs. Some payment methods have rejections such as the service provider is no longer with the payee, the payment may be refused by the payee such as with a stored value card, the payee may have changed banks and the financial instrument is not valid, and the like. A rejection of a payment causes the payer to seek an alternative payment method. An alternative payment method can have a different format for either or both the financial instrument and the EOBs, and force a payer to a different system with tracking and continual prevention of co-mingling funds between multiple systems.

The present application provides a new and improved automated payment system with an intelligent router of payments which overcomes these problems and others.

SUMMARY

In accordance with one aspect, a method of paying medical claims uses one or more processors to receive a payer payment method preferences which include an order of payment methods to each payee. A payment method is formatted and includes a consolidated financial instrument and at least one explanation of explanation of benefit associated with the consolidated financial instrument. The consolidated financial instrument transfers accumulated monies without co-mingling funds in compliance with ERISA regulations. The at least one associated explanation of benefit includes a patient identification, a payer identification, a service provider identification, a date of service, a service identification, and an amount paid. The formatted payment method are periodically sent to each payee with a coordinated transfer of the consolidated financial instrument and the at least one associated explanation of benefits. The steps of formatting and sending the payment method are repeated for each method preference in order until the transfer is accepted by each payee. The acceptance of the consolidated financial instrument and the at least one associated explanation of payment to each payee is recorded in a data store.

In accordance with another aspect, a medical claims payment system includes one or more servers configured to receive a payer payment method preferences which include an order of payment methods to each payee. A payment is formatted and includes a consolidated financial instrument and at least one explanation of explanation of benefit associated with the consolidated financial instrument. The consolidated financial instrument transfers accumulated monies without co-mingling funds in compliance with ERISA regulations. The at least one associated explanation of benefit includes a patient identification, a payer identification, a service provider identification, a date of service, a service identification, and an amount paid. The formatted payment is sent to each payee with a coordinated transfer of the consolidated financial instrument and the at least one associated explanation of benefits. The steps of formatting and sending each payment for each payment method is repeated in order until the transfer is accepted by each payee. Acceptance of the payment method to each payee is recorded in a data store.

In accordance with another aspect, a medical claims payment system includes one or more servers configured to periodically format and send payments to one or more payee by specified payment methods in an order of payer preference until each payment is accepted. The payments include a consolidated financial instrument and at least one explanation of explanation of benefit associated with the consolidated financial instrument. The consolidated financial instrument transfers accumulated monies without co-mingling funds in compliance with ERISA regulations. The at least one associated explanation of benefit includes a patient identification, a payer identification, a service provider identification, a date of service, a service identification, and an amount paid. Acceptance of the payment by each payee is recorded in a data store.

One advantage is that it reduces the number of paper checks processed and is particularly amenable to electronic funds transfers.

Another advantage resides in the standardization of information regarding benefits which are the responsibility of the insurance company and benefits which are the responsibility of the patient.

Another advantage resides in reduced processing of insurance payments by medical providers.

Another advantage resides in the improvement of patients' understanding of their medical coverage.

Another advantage is that it helps assure that charges and payments are properly applied.

Another advantage is the seamless processing of multiple payment methods.

Another advantage is the automatic routing of payments to payees.

Another advantage is an ordering of payer preferred payment methods for an optimized cost structure.

Another advantage resides in the ease of introducing new payment methods to payees based on new financial instruments.

Another advantage is the use of a single payment from one payer with multiple employer groups within ERISA regulations.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
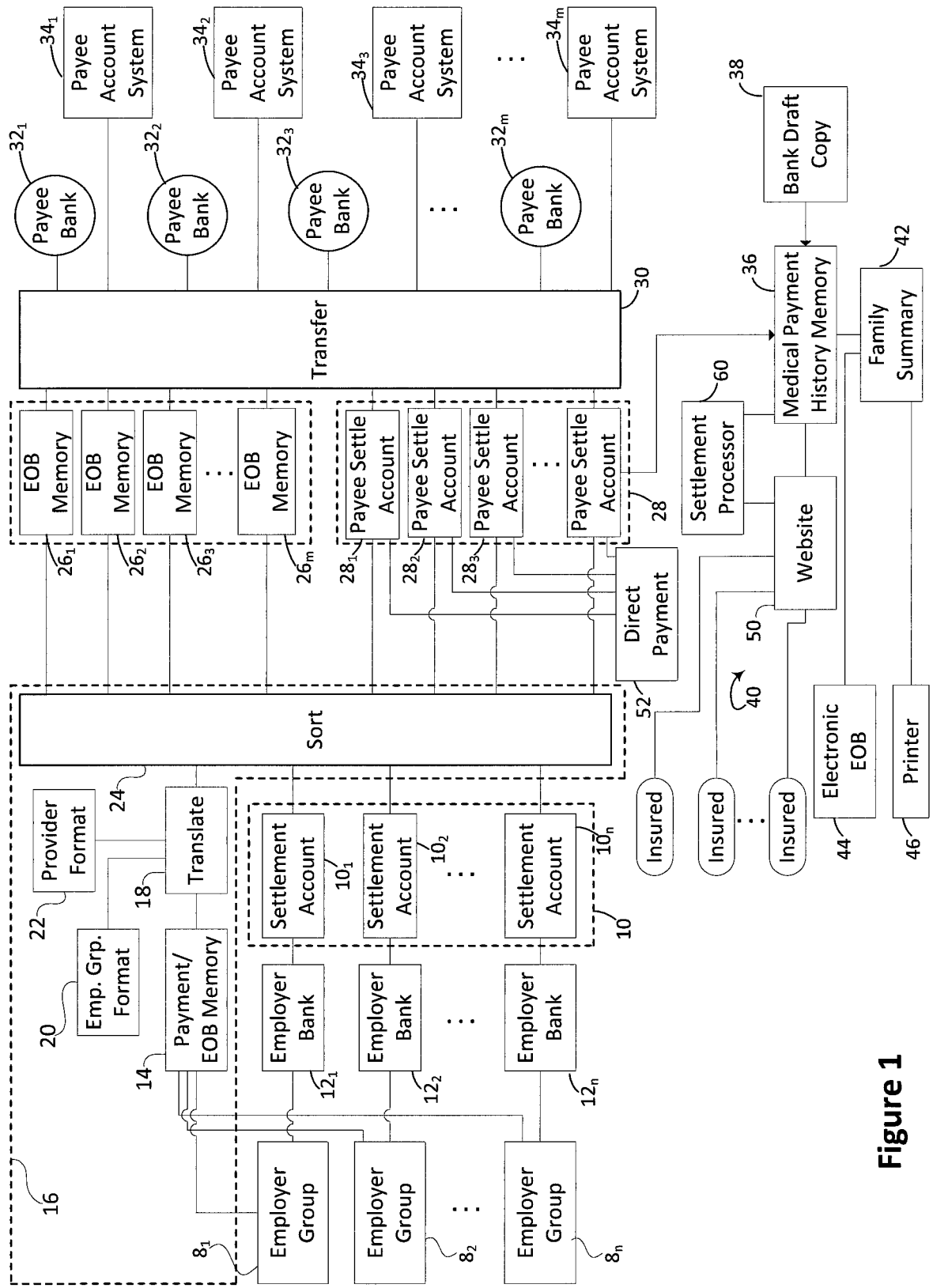
FIG. 1 is a diagrammatic illustration of an automated claim processing system in accordance with the present invention.

A plurality of employer groups $8_1, 8_2, \ldots 8_N$, each have a corresponding health insurance policy which specifies coverage, co-payments, other patient responsibilities, and the like. Each of the employer groups is associated with one or more traditional insurance carriers. For employer groups that are partially self-insured or self-funded, the employer is typically a co-insurer with an insurance company. Conversely, a common insurance carrier may underwrite several employer groups.

A series 10 of N segregated employer group settlement accounts $10_1, 10_2, \ldots 10_N$, are each associated with one of the employer groups. Typically, each employer settlement group is associated with one settlement account. In some instances, such as with co-insurance or multiple insurance carriers, an employer settlement group might be associated with two or more settlement accounts. However, each settlement account is associated with only one employer group except with a completely self-insured employer where multiple employer groups can share one settlement account. More specifically, the employer group settlement accounts are segregated accounts which are each accessible to the corresponding employer group, but not to other employer groups. Creditors of one employer group cannot reach the settlement accounts of other employer groups to avoid violations of the prohibition of co-mingling of funds. The array of settlement accounts are preferably with a common financial institution for funds transfer simplicity, but can also be with different institutions. In the instance of a completely self-insured or self-funded employer a single settlement account is permissible for multiple employee groups if individual checks are written for each group.

Each employer group adjudicates medical claims of its members and periodically, e.g., weekly, causes its bank $12_1$, $12_2, \ldots 12_N$ to issue a payment for all of the adjudicated claims of the employer group into the corresponding employer group's settlement account and sends an electronic description of the payments to a common payment memory 14. More specifically, each employer group sends Explanations of Benefits (EOBs) explaining the benefits paid, the patient information, the medical service provider information, and the like, for each of the batch of adjudicated claims. A common EOB memory 14 can store the payment descriptions of multiple payers without violating co-mingling rules. A payment allocation comparator routine or processor 16 includes an EOB translating routine or processor 18 which translates each of the EOBs from the form, format, and content of the employer group to a preferred form, format, and content of the service provider that is identified on each electronic EOB as having provided the service(s). The EOB translating routine or processor 18 resolves semantic ambiguities with a received EOB such as interpretation of "non-covered" and "pending", secondary coverage, and the like. The EOB translating routine resolves the financial transaction as a balanced transaction whereby the billed amount is completely allocated to payment amount, adjustments, and patient obligation.

The electronic EOBs stored in the EOB memory 14 are preferably segregated or at least identified by employer group. The translator routine 18 accesses an employer group content memory 20 to identify the form, format, and content of the EOB corresponding to each employer group and addresses a medical provider form, format, and content memory 22 to determine the form, format, and content preferred by each of the multiplicity of medical service providers. Because many medical service providers have a very high percentage of their medical claims paid by Medicare, they are well-equipped to handle the form, format, interpretation, and content used by Medicare. Accordingly, this form, format, interpretation, and content is often, but not always, preferred by medical service providers.

A sorting routine or processor 24 sorts the translated EOBs into a series 26 of EOB memories $26_1, 26_2, \ldots, 26_M$, each EOB memory corresponding to one of M payees. Concurrently, the sort routine 24 transfers the amount of money specified on each EOB individually from the employer group settlement account of the corresponding employer group to a one of a plurality of payee settlement accounts $28_1, 28_2, \ldots, 28_M$ corresponding to the payees of the identified service providers. More specifically, the money is transferred by a series of electronic funds transfers. More preferably, all of the payee settlement accounts 28 and all of the employer group settlement accounts are all located in the same banking institution to simplify and expedite the numerous monetary transfers.

A transfer processor or routine 30 periodically transfers the monies in the payee settlement account $28m$ corresponding to each medical service provider to their normal business bank account $32_1, 32_2, \ldots, 32_M$ which is typically in another banking institution. Although the transfer processor or routine 30 preferably makes electronic transfers on a periodic basis, e.g., daily, twice weekly, weekly, the transfer processor or routine 30 may also transfer the money by printing a bank draft. To avoid co-mingling problems, the transfer means uses a bank draft which is payable on presentation as opposed to a check which is payable when received. Concurrently, the transfer processor or routine 30 transfers the translated electronic EOBs from the set 26 of EOB memories to the electronic accounting systems $34_1, 34_2, \ldots 34_M$ of the payees. In this manner, all of the payments are maintained separated and not co-mingled until they become the property of the medical service provider or the payee for the medical service provider.

Concurrently, the transfer processor or routine 30 transfers the EOB and electronic funds transfer information to a medical payment history memory 36 which maintains a record of the EOB information, payments made, electronic transfer and routing information, and the like, which can be used to verify payment of the monies and trace such payments. If the transfer processor or routine transfers the funds by draft, the payment history memory 36 also records the draft number. Preferably, a draft copying means 38 copies each of the drafts when they are returned and cleared by the banking institution holding the payee settlement accounts. This copying may be the copying system which banks typically use currently, or may a redundant operation. The copies of the cashed drafts are transferred to the payment history memory for storage in conjunction with the corresponding payment information to provide a traceable history that the payment was, in fact, made and deposited. The medical payment history memory is preferably accessible on a read-only basis by both employer group insurers, payees and medical service providers to check and confirm payments.

A direct consumer interface system 40 enables patients to access their own medical payment records, receive EOBs and payment notices on-line, and to pay patient responsibility portions of the bill on-line. More specifically to the preferred embodiment, a family summary processor or routine 42 groups new EOBs in the payment history memory 36 by patient and, more specifically, by groups of all of the patients within a single insured's family. An electronic transfer routine or processor 44 e-mails all new family EOBs to the insured patient or other designee on a periodic basis. For example, new EOBs are sent on a weekly basis, monthly basis, or other appropriate basis. For insureds who prefer paper EOBs to electronic copies, a printing and mailing system 46 prints the new EOBs for each family group and sends them by post.

The e-mail reporting of the EOB can be done in the conventional EOB form, format, and content of the employer group, or in a standardized EOB format which more clearly specifies the amounts paid to the service providers, the amounts required to be written off, and the amount which is the patient's responsibility.

A patient accessible website 50 is accessible electronically, preferably via the internet, by individual patients. Through the website 50 using a hyper-text transfer protocol (https) configured server, the patient can check theirs and their family's medical payment histories through the medical payment history memory 36. Preferably, the website 50 is linked to a direct payment website 52. Through the direct payment website, the patients can make internet payment transactions, e.g., by credit card, to transfer funds to cover the patient responsibility portion of the medical services directly to the payee settlement accounts 28. The website 50 or the direct payee payment site 52 also sends the corresponding patient and EOB information to the corresponding EOB memories. Preferably, the direct payment site pays multiple medical service provider payee payment settlements accounts with a single credit card or other electronic money transfer operation of the patient.

Optionally, a computer-based collection processor 60 under contract with all or selected medical service providers or payees searches the medical payment memory 36 for delinquent and overdue accounts. The collection routine electronically compares the payment history and amounts due with compromise criteria and compromise limitations provided by the corresponding medical service provider(s). Based on these guidelines, the collection/settlement routine e-mails or mails by post, an offer to compromise the patient responsibility portion of the outstanding medical claims in exchange for immediate payment. Alternately, the information can be printed out or displayed for a human collections officer, who makes the offers by telephone. Upon receipt of the payments, the credit and collection routine includes a subroutine for forwarding the payment and write-off information to the corresponding EOB memories 26, and for transferring the collected monies (less a commission) to a sub-account of the corresponding payee settlement account. The commission is transferred to a separate collection commission account.

Figure 2:
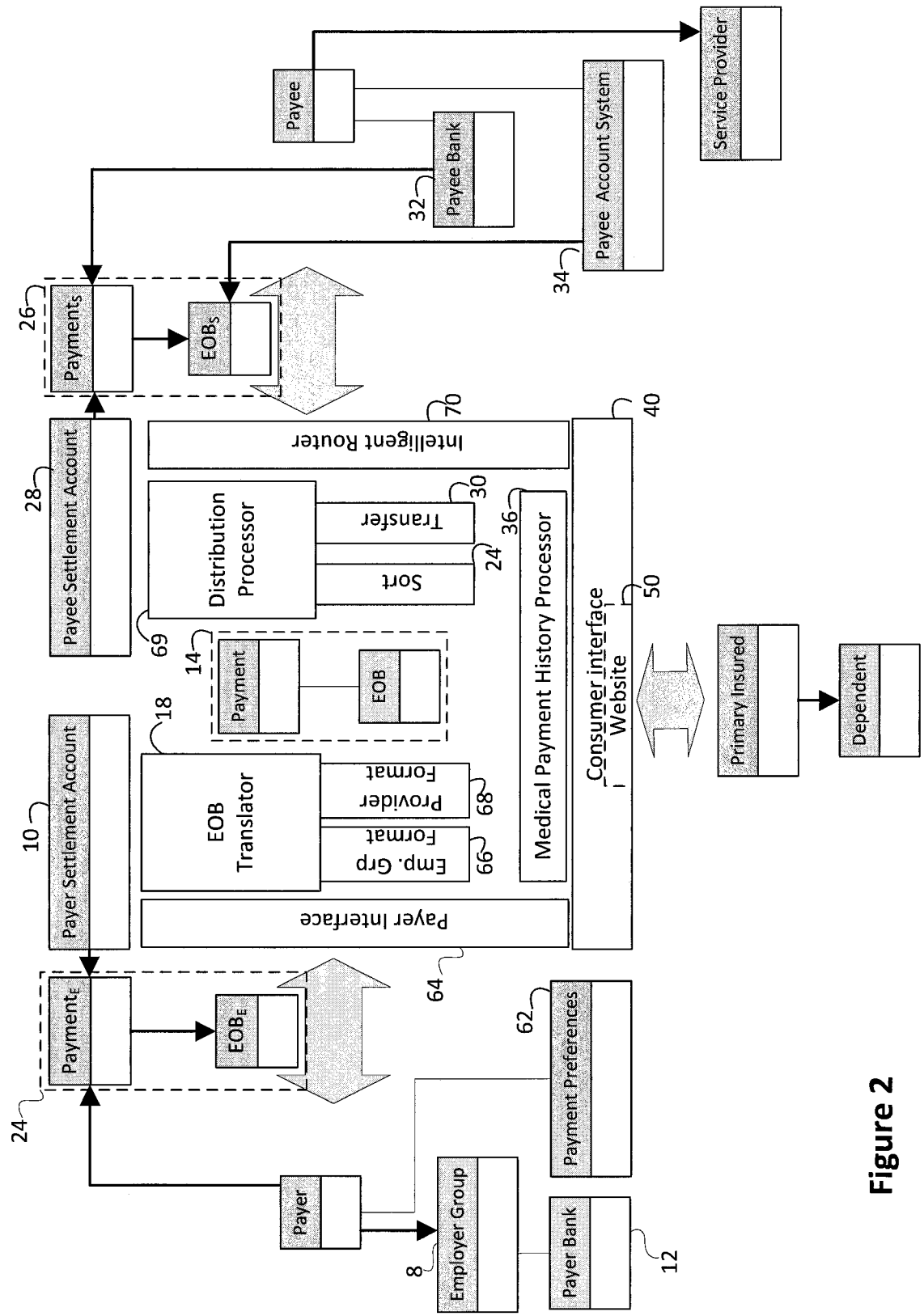
FIG. 2 is a diagrammatic illustration of the system using entity-relationship and system block diagrams in accordance with one embodiment.

FIG. 2 is a diagrammatic illustration of the system using entity-relationship and system block diagrams in accordance with one embodiment. A payer enters payment method preferences 62 through a payer interface 64. The payment method preferences 62 include an order of payment method preferences. A default order can be specified based on estimated transaction costs. The payer interface 64 includes a display window such as a browser window and a system interface which includes a server to server transmission. The payment method preferences can also default from the a system preference.

The EOB translator 18 includes two sub-modules: an employee group format module 66 which accesses the employer group content memory 20; and a provider format module 68 which accesses the provider content memory 22.

The EOB translator resolves semantic ambiguities with the received EOB from the employer group and stores the semantically resolved EOB in memory 14. The semantically resolved EOB will be sent to the payee and recorded by the medical payment history processor 36. The employer group format module 66 provides contract information to resolve such items as "non-covered" and "pending". The translator includes resolving the party responsible for each amount. The translator 18 in the provider format module 68 translates the content with the semantically resolved EOBs into the preferred format of the medical service provider with explanations and terms relative to the contract of the service provider and terms of art used in the medical specialty.

A distribution module 69 uses the sort processor 24 and the transfer processor 30 to distribute the funds and associated EOBs received from the payer to the settlement accounts 28 and the associated EOB memories 26 as described with reference to FIG. 1. Distribution of funds and tracking of the associated received EOBs follow ERISA rules. Funds are not co-mingled during the distribution or in the settlement accounts.

An intelligent router 70 formats the financial instrument and associated EOBs according to each payment method and sends the payment to the payee of each service provider. Each payment method includes a consolidated financial instrument and the associated EOBs. The associated EOBs are the semantically resolved EOBs translated into the preferred content of the medical service provider. The intelligent router formats the translated semantically resolved EOBs according to the payment method format. The consolidated financial instrument provides the movement of monies between the settlement account 28 of the payee which can include multiple service providers and the payee bank 32 without co-mingling funds in violation of ERISA rules. In one payment method, the sending of the associated EOBs includes a transfer of the EOBs and cross reference to the accounting system of each payee. More generally with all payment methods, the associated EOBs are transferred to the payee according to the format of a payment method. Each payment method has an associated cost structure including both direct and indirect costs. Different payees accept different payment methods. In addition, a payee can accept a payment method, but reject a particular payment. Furthermore, a certain percentage of claims processing associated with each payment method are completed which affects the overall cost of claims settlement.

The consumer interface 40 provides access to the medical payment history processor 36 which includes a data store of claims. The data store of claims includes the payment and translated EOBs. The translated EOBs are the received EOBs for which the EOB translator 18 has resolved semantic ambiguities. The website 50 includes one or more web servers (e.g. hyper-text transfer protocol servers) which provide access to claims for a primary insured and dependents grouped as a family unit.

Figure 3:
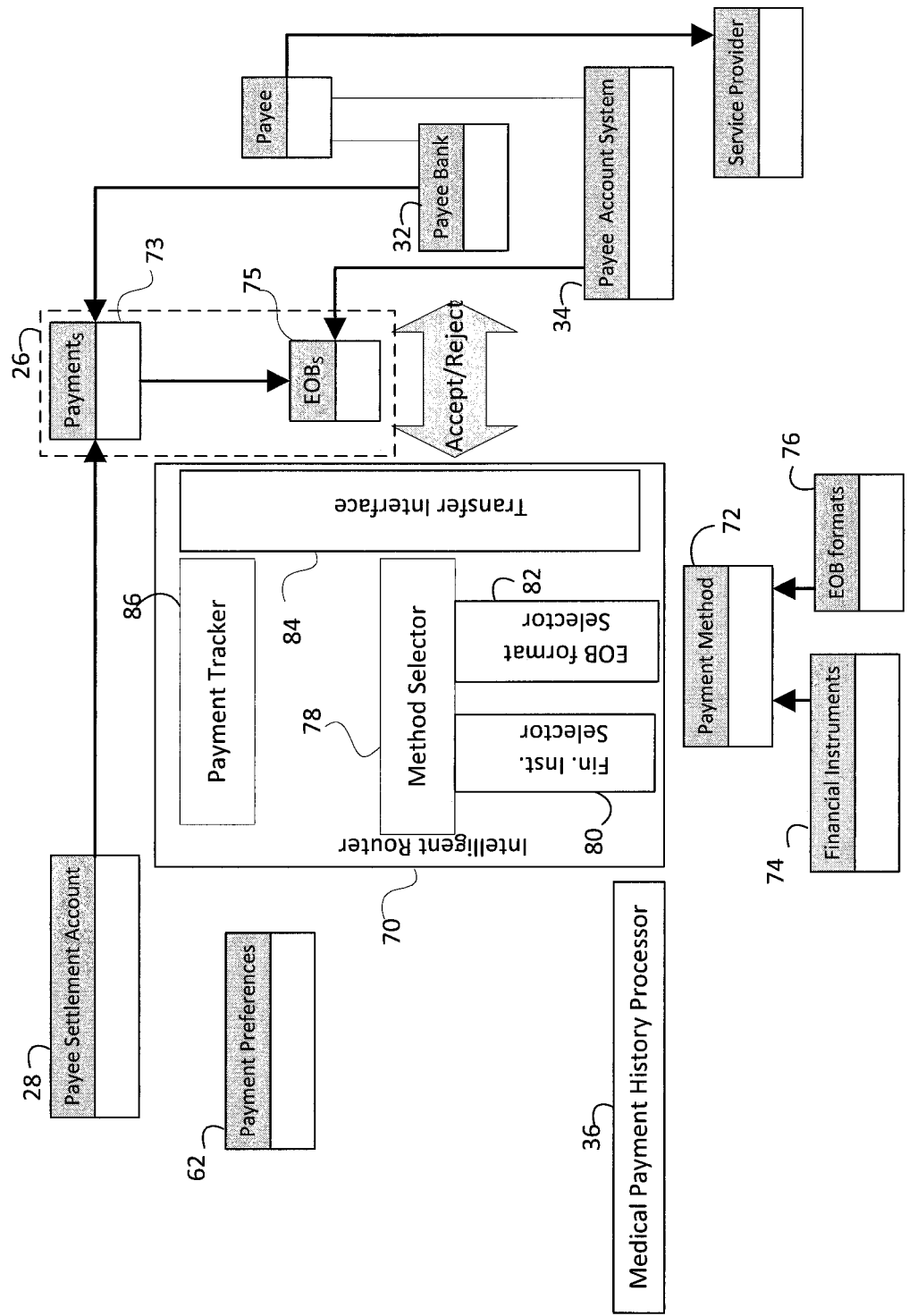
FIG. 3 illustrates the system processing of payments using an intelligent router of payment methods with entity-relationship and system block diagrams in one embodiment.

FIG. 3 illustrates the system processing of payments using an intelligent router 70 of payment methods with entity-relationship and system block diagrams in one embodiment. A payment method 72 includes a selected type of consolidated financial instrument 74 and one or more associated EOBs in a particular format 76. A type of consolidated financial instrument 74 such as an ACH ANSI ASC X12 format transfer, a Fed wire transfer, a Clearinghouse Interbank Payment (CHIPS), a bank draft, and the like, and can be used in multiple payment methods 72. There are multiple EOB formats 76 such as ANSI 835, PDF image, print image, custom formats, and the like. The EOB format 76 can be used in multiple payment methods 72. However, one payment method 72 can used only one type of consolidated financial instrument 74 and one type of EOB format 76. In addition, the type of consolidate financial instrument 74 can limit the permissible EOB format 76.

The intelligent router 70 selects one payment method 72 based on the payment preferences 62 using a method selector module 78. The method selector module 78 formats the payment by formatting the financial instrument according to the selected payment method using a financial instrument selector module 80. The method selector module 78 formats the one or more associated EOBs according to the selected payment method using the EOB format selector module 82. If the payee does not accept the payment method, the method selector module 78 bypasses that payment method for that payee and proceeds to the next payment method in order of preference. The router sends the formatted payment using a transfer interface 84 which handles the communication protocol for the particular payment. The transfer interface 84 interacts with the payee devices which accept the transfer of both funds and associated EOBs. The transfer interface 84 notifies a payment tracker 86 of the status of the transfer. The transfer interface 84 receives any rejections from the payee. The payment tracker 86 keeps track of the status or what claims have been sent by which method and whether they are accepted. If a rejection is received by the transfer interface, then the payment tracker is notified. If the payment tracker 86 receives a rejection, then the method selector 78 selects the next method in order of preference based on the payment preferences 62 and begins the process of formatting another financial instrument and another associated EOBs using the financial instrument selector 80 and the EOB format selector module 82. The router will repeat the process for each payment method until all funds and claims are accepted by the payee. The payment tracker 86 keeps track of sent payments and the payment method employed. The process of tracking payment methods, receiving rejections, and moving to the next preferred payment method is automatic and computer implemented.

As new financial instruments and or EOB formats are developed, new payment methods are easily added to the router. A new financial instrument is defined and/or a new EOB format is defined as plug compatible using the financial instrument selector module 80 and/or the EOB format selector module 82. The method selector module 78 defines the payment methods which incorporate the new instrument format or EOB format. Preferences can be updated to incorporate the new payment methods as contracts, and/or costs constraints permit.

Figure 4:
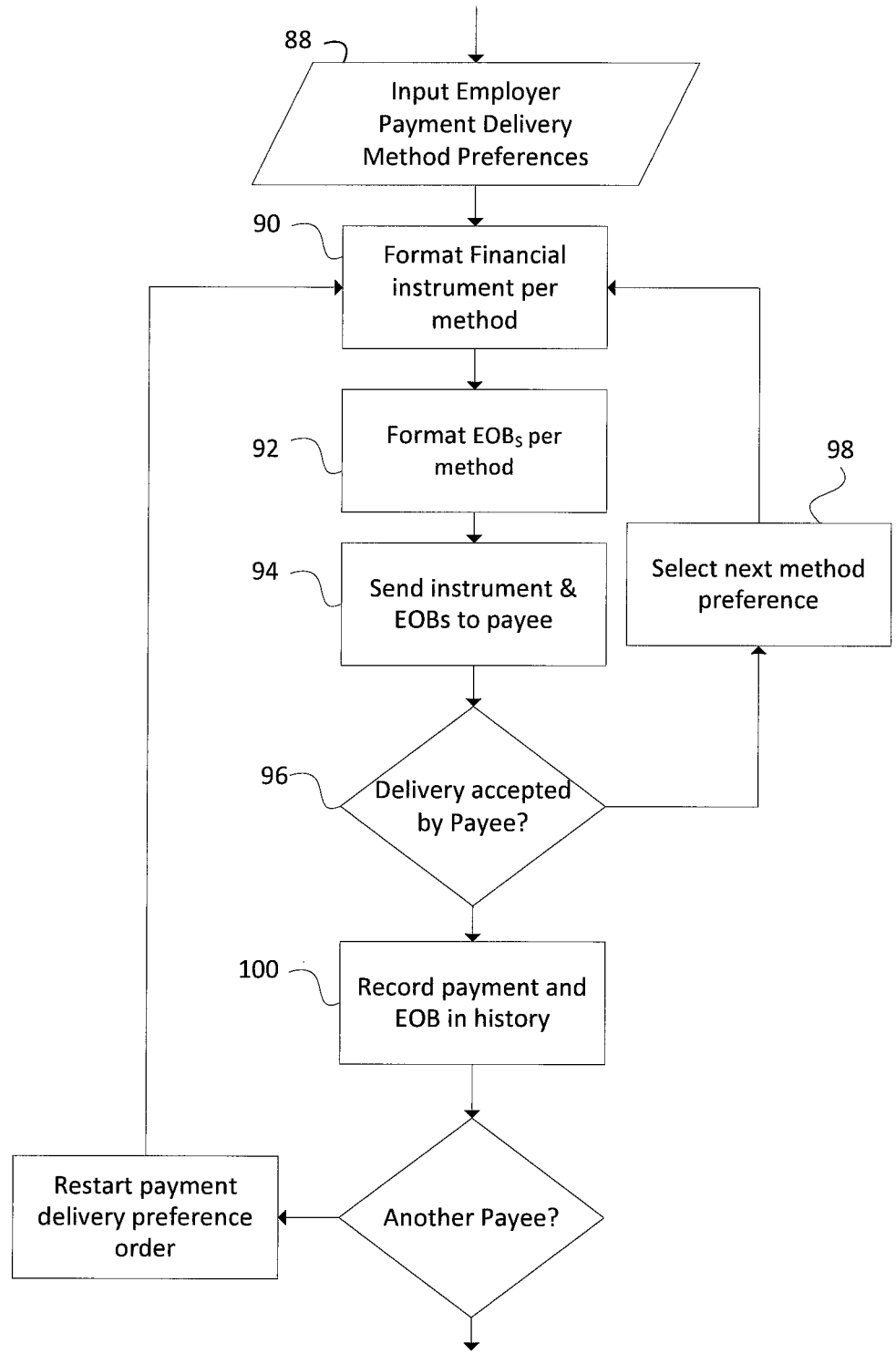
FIG. 4 is a flowchart which illustrates the processing steps of the intelligent router in one embodiment.

FIG. 4 is a flowchart which illustrates the processing steps of the intelligent router in one embodiment. The method is implemented by one or more routers. The payment method preferences 64 are input through the payer interface 64 in a step 88 or by default from the system. In a step 90, the financial instrument selector module 80 formats the financial instrument into the format according the payment method. The EOB selector format module 82 formats the associated EOBs into the payment format in a step 92. The payment formatted according to the payment method 72 is sent in a step 94 by the transfer interface which is a coordinated transfer of both the formatted financial instrument and the formatted associated EOBs. The payment tracker 86 keeps track of the payment. If a delivery rejection is received through the transfer interface 84 in a step 96, then the payment tracker notifies the method selector module 78 to select another method for the rejected claims and funds in a step 98. The process is repeated using each payment method until the claims and funds are accepted. Once the payment method is accepted in the step 96, then the payment is recorded by the medical history payment processor 36 in a step 100. Once a payment is accepted, further payments from the same payer to the same payee can be made using the accepted payment method for a selected duration. Also, the intelligent router can remember, for a selected duration, rejected payment methods for each payee to expedite payment attempts from other payers.

The process of sending payments by the intelligent router to each payee can be repeated for other payees according to the payer payment preferences. The steps can occur in parallel between payees or serially. The process can occur with different periods such as hourly, daily, weekly, on demand, and the like depending upon the payment methods.

Figure 5:
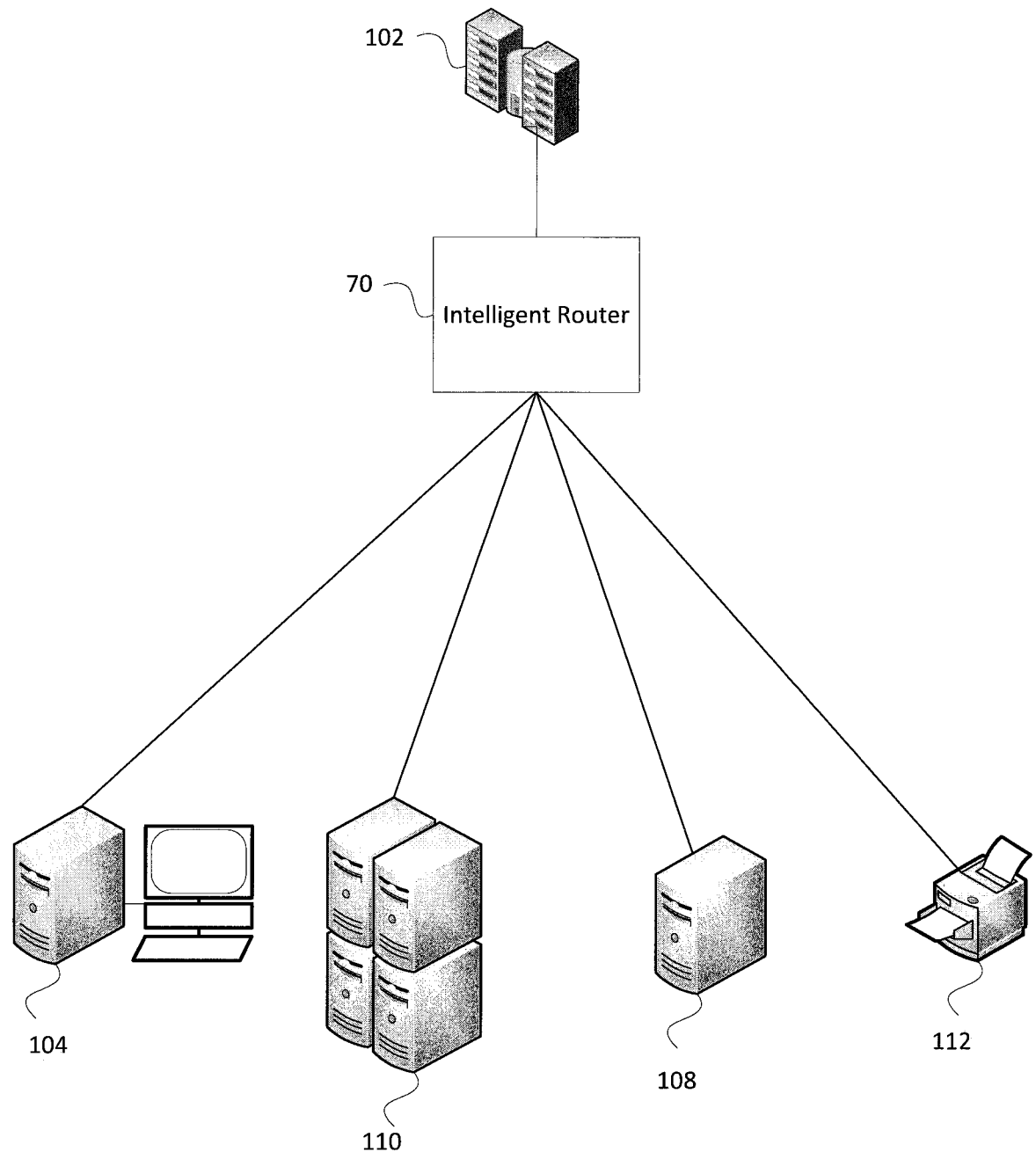
FIG. 5 diagrammatically shows one embodiment of the intelligent router multiple payment method components.

FIG. 5 diagrammatically shows one embodiment of the intelligent router 70 with multiple payment method components. The intelligent router 70 operates on one or more processors distributed across one or more servers. Attached to the intelligent router is electronic storage 102. Attachment can be performed in a variety of means such as direct attachment, network attached storage, network accessible storage, remote storage and the like. Performance and cost considerations apply to the amount and type of storage. The intelligent router storage 102 can be organized at the file level, object level, database level or a combination of any of these. Devices which support format of the financial instrument and the EOB are also attached. Each of these attachments can be direct, network, virtual private network, or Internet based. The financial instrument and EOBs are cross referenced payments are periodic and the frequency varies by the payer and the payment method preferences. Four options are presented in one embodiment, but more are possible.

As financial instruments are developed and alternative formats of electronic transfer occur, additional methods are added. The intelligent router tracks the order of payment methods, funds, and EOBs. If a rejection is received using one method, a transaction is automatically formatted using the next preferred method for both the financial instrument and the associated EOBs and the transaction sent. If the payee or service provider does not accept a particular method, the router bypasses that method for those funds and EOBs and processes the next valid payment method.

One type of payment method includes a format and transmission to another server or combination of servers dedicated to a payee or a service provider 104. Typically one server is used, but separate servers can be used with one typically involved with in the financial instrument transfer, and another server dedicated to receipt of EOBs. The financial instrument is a consolidated ACH transfer which moves the funds electronically and is formatted according to ACH CTX rules which include ANSI ASC X12 formats and comply with ERISA. The EOBs translated to the EOB of the payee are formatted using ANSI 835 open form format. Typically, there is a low fee with this type of payment and there are no rejections. However, there are few organizations that have the processing sophistication to provide a direct transfer.

A second payment method uses a stored value card such as a credit card, a debit card and the like. The financial transfer is accomplished electronically using one of several stored value service provider electronic transfer methods. The format of the electronic funds transfer method is specified by the stored value service provider. EOBs are transmitted electronically to a fax machine or fax server 108. A stored value card and associated faxed EOBs do not incur print or mailing costs to the payer, and there are typically basis points charged to the provider. However, acceptance is voluntary and rejections occur.

A third payment method involves the use of a contracted ACH provider network 110. Similar in operation to a direct provider, a third party representative houses the server. With this option separate payments for multiple payees from one payer are consolidated. The third party representative provides the distribution of funds to each payee or service provider. However, fees to the payer are imposed reducing the desirability of this option which is reflected in payer provider preferences. In addition, not all service providers are represented, and some rejections occur.

A fourth option in this embodiment includes a default option which is to create a consolidated draft payment and a printed statement. A print device 112 is used to print the draft payment and the printed statement. The cost to print is low, but handling and tracking costs for payees is high primarily due to labor costs. This typically occurs for smaller providers which do not subscribe to any other method of payment. The consolidated bank draft is payable upon presentation and includes cross reference to EOBs to comply with ERISA regulations. The printing occurs using a printer attached via a network or print server.

It is to be appreciated that in connection with the particular exemplary embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

We claim:

1. A computer implemented method of paying adjudicated medical claims to medical service providers in compliance with the Employment Retirement Income Security Act (ERISA) prohibition of co-mingling of health insurance payments, comprising:

using one or more processors:
a health insurance payment system electronically receiving a plurality of groups of a plurality of explanation of benefits (EOBs) for a plurality of respective health insurance payments of a plurality of adjudicated medical insurance claims, each group of EOBs from one of a plurality of payors, and each payor associated with one of a plurality of employer groups, and the health insurance payment system electronically receiving monies from each of the plurality of payors and depositing the received monies into a plurality of respective employer group settlement accounts of at least one financial institution with the employer group settlement accounts segregated by employer group and insurance carrier, and each associated EOB received in a memory associated with the one or more processors, each associated EOB including at least one adjudicated claim for one patient and one medical service provider and identification of a portion of the received monies allocated to the at least one adjudicated claim;
the health insurance payment system segregately storing each associated EOB in an associated memory;
the health insurance payment system including an EOB translator associated with an employee group format module and associated with a provider format module with each accessing associated content memory, wherein the translator and the associated employee group format module resolve semantic ambiguities and allocate a medical service provider billed amount to at least one of the respective health insurance payment amount, an adjustment amount and a patient obligation amount associated with each EOB stored in the associated memory from a received form, format, and content of the employer group; and the EOB translator and associated provider format module translate each associated semantically resolved EOB stored in the associated memory from a received form, format, and content of the employer group to a preferred payee form, format, and content of the one medical service provider in the associated EOB;
the health insurance payment system concurrently electronically transferring monies from the plurality of employer group settlement accounts of the at least one financial institution to a plurality of service provider settlement accounts at the at least one financial institution associated with the respective employer group without co-mingling funds to accumulate monies from a plurality of the plurality of employer group settlement accounts in each service provider settlement account and sorting the translated EOBs by medical service provider, each service provider settlement account corresponding to one medical service provider, each electronic transfer of money from one employer group settlement account to one service provider settlement account based on the identified portion of monies in each EOB allocated to adjudicated claims of the corresponding one medical service provider; and
the health insurance payment system electronically and concurrently transferring accumulated monies from the service provider settlement accounts to bank accounts of the medical service providers without co-mingling funds and transferring translated EOBs to electronic accounting systems of medical service providers, wherein electronically transferring of accumulated monies are payments maintained separated until the payment becomes the property of the medical service provider, wherein transferring of monies to each bank account of the medical service provider and transferring translated EOBs to each medical service provider includes a single consolidated payment from a single payor including a plurality of health insurance payments of a plurality of adjudicated medical insurance claims transferred from a single service provider settlement account to the bank account of the medical service provider and a plurality of translated EOBs associated with the single consolidated payment.

2. The computer implemented method according to claim 1, wherein the form, format, and content of the received associated EOBs includes ANSI 835 format.

3. The computer implemented method according to claim 1, wherein the translator determines a co-pay of the patient based on at least one of a non-covered amount or a pending amount.

4. The computer implemented method according to claim 1, wherein the translator determines a write-off amount based on at least one of a non-covered amount or a pending amount.

5. The computer implemented method according to claim 1, wherein the translator determines an amount to be billed to the patient based on a non-covered amount or a pending amount.

6. The computer implemented method according to claim 1, wherein a payment of the transferred monies includes a financial instrument issued by an issuing bank.

7. The computer implemented method according to claim 6, wherein the instrument includes at least one of a bank draft, a credit card, a debit card, or a stored value card.

8. The computer implemented method according to claim 1, further comprising:
recording the receiving and transferring of monies and associated EOBs in a medical payment history memory.

9. The computer implemented method according to claim 8, further comprising:
tracing the record receipt and transfers of monies and the associated EOBs from receipt in the employer group settlement account and EOB memory to the bank account and electronic accounting system of the medical service provider.

10. The computer implemented method according to claim 1, wherein the translator determines an amount to be written off and an amount for which the patient is responsible based on a received pending amount or a received non-covered amount and further comprising:
emailing EOBs of the adjudicated claims for a family to a patient which specifies each amount paid to the service providers, the amounts required to be written off, and the amount for which the patient is responsible.

11. The computer-implemented method according to claim 1, wherein a payment of the transferred monies includes a financial instrument issued by an issuing bank and the financial instrument is a stored value card.

* * * * *